(12) United States Patent
Zucherman et al.

(10) Patent No.: US 7,837,734 B2
(45) Date of Patent: *Nov. 23, 2010

(54) SYSTEM AND METHOD FOR REPLACING DEGENERATED SPINAL DISKS

(75) Inventors: James F. Zucherman, San Francisco, CA (US); Ken Y. Hsu, San Francisco, CA (US); Charles J. Winslow, Walnut Creek, CA (US); Scott A. Yerby, Montara, CA (US); John J. Flynn, West Milford, NJ (US); Steven T. Mitchell, Pleasant Hill, CA (US); John A. Markwart, Castro Valley, CA (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 485 days.

This patent is subject to a terminal disclaimer.

(21) Appl. No.: 11/734,681

(22) Filed: Apr. 12, 2007

(65) Prior Publication Data
US 2007/0191955 A1    Aug. 16, 2007

Related U.S. Application Data

(62) Division of application No. 10/730,717, filed on Dec. 8, 2003, now Pat. No. 7,217,291.

(51) Int. Cl.
*A61F 2/44* (2006.01)
(52) U.S. Cl. .................................... 623/17.15
(58) Field of Classification Search ... 623/17.11–17.16, 623/16.11; 606/246, 60
See application file for complete search history.

(56) References Cited

U.S. PATENT DOCUMENTS

| | | | |
|---|---|---|---|
| 2,677,369 A | 5/1954 | Knowles | |
| 3,648,691 A | 3/1972 | Lumb | |
| 3,867,728 A | 2/1975 | Stubstad et al. | |
| 3,875,595 A | 4/1975 | Froning | |
| 3,904,226 A * | 9/1975 | Smalley | 280/486 |

(Continued)

FOREIGN PATENT DOCUMENTS

DE   3113142   1/1982

(Continued)

OTHER PUBLICATIONS

International Search Report, PCT Appln. No. PCT/US03/27109, mailed May 12, 2004, 6 pages.
International Search Report, PCT Appln. No. PCT/US03/33942, mailed Aug. 27, 2004, 6 pages.
International Search Report, PCT Appln. No. PCT/US03/33884, mailed Jan. 25, 2005, 5 pages.

(Continued)

*Primary Examiner*—Alvin J Stewart

(57) ABSTRACT

A system and method for replacing degenerated spinal disks in accordance with the present invention can substitute for interbody fusion techniques by replacing degenerated spinal disks with artificial spinal disks. In one embodiment, the system can comprise one or more artificial spinal disks, each comprising an upper and lower housing, a first spacer and a second spacer partially enclosed by a cavity formed by the housings, and a shaft with a spring positioned between the first spacer and the second spacer such that the spacers are urged apart.

20 Claims, 16 Drawing Sheets

U.S. PATENT DOCUMENTS

| | | | |
|---|---|---|---|
| 4,309,777 A | 1/1982 | Patil | |
| 4,349,921 A | 9/1982 | Kuntz | |
| 4,759,766 A | 7/1988 | Büttner-Janz et al. | |
| 4,759,769 A * | 7/1988 | Hedman et al. | 623/17.13 |
| 4,772,287 A | 9/1988 | Ray et al. | |
| 4,863,476 A | 9/1989 | Shepperd | |
| 4,863,477 A | 9/1989 | Monson | |
| 4,874,389 A | 10/1989 | Downey | |
| 4,878,915 A | 11/1989 | Brantigan | |
| 4,904,260 A | 2/1990 | Ray et al. | |
| 4,911,718 A | 3/1990 | Lee et al. | |
| 4,932,969 A | 6/1990 | Frey et al. | |
| 4,946,378 A | 8/1990 | Hirayama et al. | |
| 4,997,432 A | 3/1991 | Keller | |
| 5,002,576 A | 3/1991 | Fuhrmann et al. | |
| 5,011,484 A | 4/1991 | Breard | |
| 5,035,716 A | 7/1991 | Downey | |
| 5,047,055 A | 9/1991 | Bao et al. | |
| 5,071,437 A | 12/1991 | Steffee | |
| 5,108,438 A | 4/1992 | Stone | |
| 5,122,130 A | 6/1992 | Keller | |
| 5,123,926 A * | 6/1992 | Pisharodi | 623/17.13 |
| 5,171,280 A | 12/1992 | Baumgartner | |
| 5,171,281 A | 12/1992 | Parsons et al. | |
| 5,192,326 A | 3/1993 | Bao et al. | |
| 5,246,458 A | 9/1993 | Graham | |
| 5,258,031 A | 11/1993 | Salib et al. | |
| 5,258,043 A | 11/1993 | Stone | |
| 5,306,307 A | 4/1994 | Senter | |
| 5,306,308 A | 4/1994 | Gross et al. | |
| 5,306,309 A | 4/1994 | Wagner et al. | |
| 5,314,477 A | 5/1994 | Marnay | |
| 5,320,644 A | 6/1994 | Baumgartner | |
| 5,370,697 A | 12/1994 | Baumgartner | |
| 5,375,823 A * | 12/1994 | Navas | 623/17.15 |
| 5,390,683 A | 2/1995 | Pisharodi | |
| 5,401,269 A | 3/1995 | Büttner-Janz et al. | |
| 5,425,773 A | 6/1995 | Boyd et al. | |
| 5,458,642 A | 10/1995 | Beer et al. | |
| 5,458,643 A | 10/1995 | Oka et al. | |
| 5,496,318 A | 3/1996 | Howland | |
| 5,507,816 A | 4/1996 | Bullivant | |
| 5,514,180 A | 5/1996 | Heggeness et al. | |
| 5,534,028 A | 7/1996 | Bao et al. | |
| 5,534,029 A | 7/1996 | Shima | |
| 5,534,030 A | 7/1996 | Navarro et al. | |
| 5,545,229 A | 8/1996 | Parsons et al. | |
| 5,549,679 A | 8/1996 | Kuslich | |
| 5,554,191 A | 9/1996 | Lahille et al. | |
| 5,556,431 A | 9/1996 | Büttner-Janz | |
| 5,562,736 A | 10/1996 | Ray et al. | |
| 5,562,738 A | 10/1996 | Boyd et al. | |
| 5,609,634 A | 3/1997 | Voydeville | |
| 5,645,596 A | 7/1997 | Kim et al. | |
| 5,645,597 A | 7/1997 | Krapiva | |
| 5,658,335 A * | 8/1997 | Allen | 623/17.16 |
| 5,665,122 A | 9/1997 | Kambin | |
| 5,674,294 A | 10/1997 | Bainville et al. | |
| 5,674,295 A | 10/1997 | Ray et al. | |
| 5,674,296 A | 10/1997 | Bryan et al. | |
| 5,676,701 A | 10/1997 | Yuan et al. | |
| 5,676,702 A | 10/1997 | Ratron | |
| 5,683,465 A | 11/1997 | Shinn et al. | |
| 5,702,450 A | 12/1997 | Bisserie | |
| 5,702,454 A | 12/1997 | Baumgartner | |
| 5,716,416 A | 2/1998 | Lin | |
| 5,755,796 A | 5/1998 | Ibo et al. | |
| 5,755,798 A | 5/1998 | Papavero et al. | |
| 5,782,832 A | 7/1998 | Larsen et al. | |
| 5,824,093 A | 10/1998 | Ray et al. | |
| 5,824,094 A | 10/1998 | Serhan et al. | |
| 5,827,328 A | 10/1998 | Buttermann | |
| 5,865,845 A | 2/1999 | Thalgott | |
| 5,865,846 A | 2/1999 | Bryan et al. | |
| 5,865,848 A * | 2/1999 | Baker | 623/17.15 |
| 5,885,299 A | 3/1999 | Winslow et al. | |
| 5,888,226 A | 3/1999 | Rogozinski | |
| 5,893,889 A | 4/1999 | Harrington | |
| 5,895,428 A | 4/1999 | Berry | |
| 5,899,941 A | 5/1999 | Nishijima et al. | |
| 5,919,235 A | 7/1999 | Husson et al. | |
| 5,928,284 A * | 7/1999 | Mehdizadeh | 623/17.13 |
| 5,964,807 A | 10/1999 | Gan et al. | |
| 5,976,186 A | 11/1999 | Bao et al. | |
| 6,001,130 A | 12/1999 | Bryan et al. | |
| 6,022,376 A | 2/2000 | Assell et al. | |
| 6,039,763 A | 3/2000 | Shelokov | |
| 6,080,193 A * | 6/2000 | Hochshuler et al. | 623/17.16 |
| 6,093,205 A | 7/2000 | McLeod et al. | |
| 6,110,210 A | 8/2000 | Norton et al. | |
| 6,113,637 A | 9/2000 | Gill et al. | |
| 6,132,465 A | 10/2000 | Ray et al. | |
| 6,136,031 A | 10/2000 | Middleton | |
| 6,139,579 A | 10/2000 | Steffee et al. | |
| 6,146,421 A | 11/2000 | Gordon et al. | |
| 6,146,422 A | 11/2000 | Lawson | |
| 6,156,067 A | 12/2000 | Bryan et al. | |
| 6,162,252 A | 12/2000 | Kuras et al. | |
| 6,165,218 A | 12/2000 | Husson et al. | |
| 6,176,882 B1 | 1/2001 | Biedermann et al. | |
| 6,190,414 B1 | 2/2001 | Young et al. | |
| 6,368,351 B1 | 4/2002 | Glenn et al. | |
| 6,454,806 B1 | 9/2002 | Cohen et al. | |
| 6,517,580 B1 * | 2/2003 | Ramadan et al. | 623/17.15 |
| 6,582,437 B2 | 6/2003 | Dorchak et al. | |
| 6,723,126 B1 | 4/2004 | Berry | |
| 6,755,841 B2 | 6/2004 | Fraser et al. | |
| 6,770,095 B2 | 8/2004 | Grinberg et al. | |
| 6,835,206 B2 * | 12/2004 | Jackson | 623/17.11 |
| 6,905,512 B2 | 6/2005 | Paes et al. | |
| 7,018,415 B1 * | 3/2006 | McKay | 623/17.15 |
| 7,052,515 B2 * | 5/2006 | Simonson | 623/17.13 |
| 7,147,665 B1 * | 12/2006 | Bryan et al. | 623/17.16 |
| 7,273,496 B2 * | 9/2007 | Mitchell | 623/17.14 |
| 7,291,171 B2 * | 11/2007 | Ferree | 623/17.11 |
| 7,331,995 B2 * | 2/2008 | Eisermann et al. | 623/17.15 |
| 7,377,921 B2 * | 5/2008 | Studer et al. | 606/248 |
| 7,473,276 B2 * | 1/2009 | Aebi et al. | 623/17.15 |
| 7,476,238 B2 * | 1/2009 | Panjabi, Manohar M. | 606/257 |
| 7,485,134 B2 * | 2/2009 | Simonson | 606/279 |
| 7,531,001 B2 * | 5/2009 | De Villiers et al. | 623/17.14 |
| 7,604,654 B2 * | 10/2009 | Fallin et al. | 606/258 |
| 7,611,538 B2 * | 11/2009 | Belliard et al. | 623/17.15 |
| 7,632,314 B2 * | 12/2009 | Dietz | 623/20.33 |
| 7,641,692 B2 * | 1/2010 | Bryan et al. | 623/17.15 |
| 7,682,376 B2 * | 3/2010 | Trieu | 606/248 |
| 7,699,875 B2 * | 4/2010 | Timm | 606/254 |
| 7,708,778 B2 * | 5/2010 | Gordon et al. | 623/17.15 |
| 7,722,674 B1 * | 5/2010 | Grotz | 623/17.11 |
| 7,727,280 B2 * | 6/2010 | McLuen | 623/17.16 |
| 2002/0022887 A1 * | 2/2002 | Huene | 623/17.16 |
| 2002/0035400 A1 * | 3/2002 | Bryan et al. | 623/17.15 |
| 2002/0040243 A1 | 4/2002 | Attali et al. | |
| 2002/0107574 A1 | 8/2002 | Boehm et al. | |
| 2002/0128716 A1 * | 9/2002 | Cohen et al. | 623/17.15 |
| 2003/0040801 A1 * | 2/2003 | Ralph et al. | 623/17.13 |
| 2004/0024461 A1 * | 2/2004 | Ferree | 623/17.13 |
| 2004/0039448 A1 * | 2/2004 | Pisharodi | 623/17.15 |
| 2004/0106998 A1 | 6/2004 | Ferree | |
| 2004/0138750 A1 | 7/2004 | Mitchell | |
| 2004/0143332 A1 * | 7/2004 | Krueger et al. | 623/17.14 |
| 2004/0172135 A1 * | 9/2004 | Mitchell | 623/17.15 |
| 2005/0278026 A1 | 12/2005 | Gordon et al. | |
| 2006/0276899 A1 * | 12/2006 | Zipnick et al. | 623/17.13 |

| | | | | |
|---|---|---|---|---|
| 2008/0077244 A1* | 3/2008 | Robinson | ............... | 623/17.16 |
| 2009/0270992 A1* | 10/2009 | Gerber et al. | ............ | 623/17.16 |
| 2010/0114318 A1* | 5/2010 | Gittings et al. | ............ | 623/17.12 |

FOREIGN PATENT DOCUMENTS

| | | |
|---|---|---|
| EP | 0322334 | 6/1989 |
| FR | 2705227 | 11/1994 |
| FR | 2722088 | 1/1996 |
| FR | 2722980 | 2/1996 |
| FR | 2724554 | 3/1996 |
| GB | 780652 | 8/1957 |
| WO | WO 01/01893 A1 | 1/2001 |

OTHER PUBLICATIONS

Supplementary European Search Report, EPO, Application No. EP 97 95 4632.2, mailed Aug. 31, 2004, 5 pages.
Supplementary European Search Report, EPO, Application No. EP 98 95 7384.5, mailed Aug. 31, 2004, 5 pages.
Supplementary European Search Report, EPO, Application No. EP 98 95 7346.4, mailed Aug. 31, 2004, 5 pages.

* cited by examiner

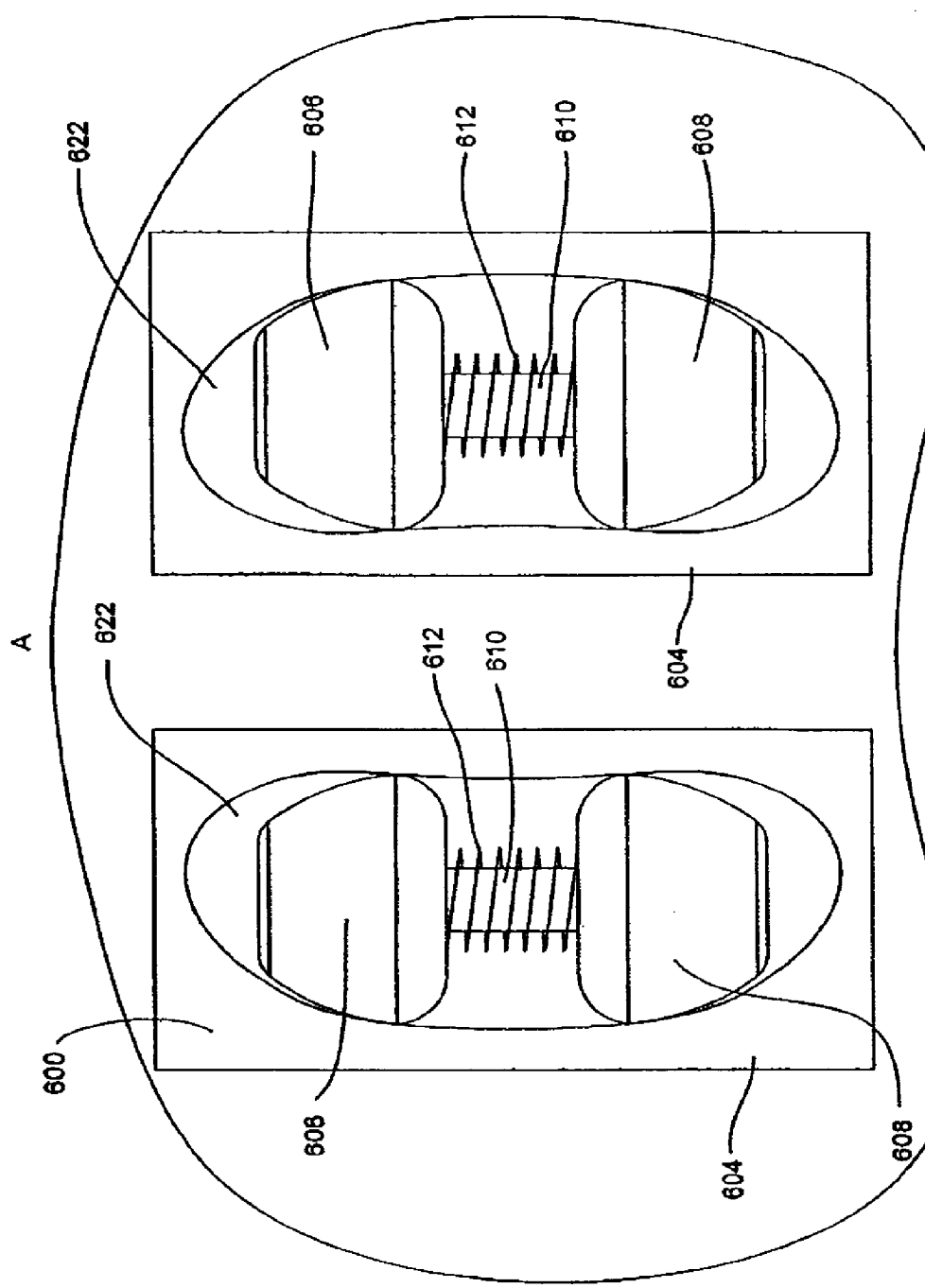

SYSTEM AND METHOD FOR REPLACING DEGENERATED SPINAL DISKS

CLAIM OF PRIORITY

This Application is a Divisional of U.S. patent application Ser. No. 10/730,717, filed Dec. 8, 2003, entitled "System and Method for Replacing Degenerated Spinal Disks", and is hereby incorporated herein by reference.

CROSS-REFERENCED CASES

The following U.S. Patent Applications are cross-referenced and incorporated herein by reference: ARTIFICIAL VERTEBRAL DISK REPLACEMENT IMPLANT WITH TRANSLATING PIVOT POINT AND METHOD, U.S. Provisional Patent Application No. 60/422,039, Inventor: James F. Zucherman et al., filed on Oct. 29, 2002; ARTIFICIAL VERTEBRAL DISK REPLACEMENT IMPLANT WITH TRANSLATING PIVOT POINT AND METHOD, U.S. patent application Ser. No. 10/684,669, Inventor: James F. Zucherman et al., filed on Oct. 14, 2003; ARTIFICIAL VERTEBRAL DISK REPLACEMENT IMPLANT WITH CROSSBAR SPACER AND METHOD, U.S. Provisional Patent Application No. 60/422,021, Inventor: Steve Mitchell, filed on Oct. 29, 2002; ARTIFICIAL VERTEBRAL DISK REPLACEMENT IMPLANT WITH CROSSBAR SPACER AND METHOD, U.S. patent application Ser. No. 10/684,668, Inventor: Steve Mitchell, filed on Oct. 14, 2003; ARTIFICIAL VERTEBRAL DISK REPLACEMENT IMPLANT WITH A SPACER AND METHOD, U.S. Provisional Patent Application No. 60/422,022, Inventor: Steve Mitchell, filed on Oct. 29, 2002; ARTIFICIAL VERTEBRAL DISK REPLACEMENT IMPLANT WITH A SPACER AND METHOD, U.S. patent application Ser. No. 10/685,011, Inventor: Steve Mitchell, filed on Oct. 14, 2003.

TECHNICAL FIELD

The present invention relates to spinal disks and spinal disk replacement devices.

BACKGROUND

A common procedure for handling pain associated with degenerative spinal disk disease is the use of devices for fusing together two or more adjacent vertebral bodies. The procedure is known by a number of terms, one of which is vertebral interbody fusion. Interbody fusion can be accomplished through the use of a number of devices and methods known in the art. These include screw arrangements, solid bone implant methodologies, and fusion devices which include a cage or other mechanism which is packed with bone and/or bone growth inducing substances. All of the above are implanted between adjacent vertebral bodies in order to fuse the vertebral bodies together, alleviating associated pain.

There are a number of drawbacks to undergoing interbody fusion. One drawback is that interbody fusion at one or more levels of the spine may cause decreased motion of the spine. Another drawback is that having interbody fusion at one or more levels of the spine may cause more stress to be transferred to adjacent levels. Transferred stress may cause new problems to develop at other levels of the spine, which may lead to additional back surgery.

Alternatives to interbody fusion surgery have been proposed including the use of artificial spinal disks. Such artificial spinal disks act like cushions or "shock absorbers" between vertebrae and may contribute to the flexibility and motion of the spinal column. Thus a purpose and advantage of such artificial spinal disks is to replace a degenerated spinal disk, while preserving the range of motion of the spine. Replacement of a spinal disk with an artificial disk may treat underlying back pain, while protecting patients from developing problems at an adjacent level of the spine.

A number of different artificial disks have been proposed. For example, one such proposal includes an artificial disk primarily comprising two metal metallic plates between which is a core that allows for motion. Another proposal includes two spinal disk halves connected at a pivot point. Other artificial disks have been proposed in the art.

BRIEF DESCRIPTION OF THE FIGURES

Further details of embodiments of the present invention are explained with the help of the attached drawings in which:

FIG. 6C is a top plan view of an alternative embodiment of the present invention showing an artificial spinal disk positioned such that a first spacer is on a left side of a patient and a second spacer is on a right side of a patient.

DETAILED DESCRIPTION

Figure 1A:
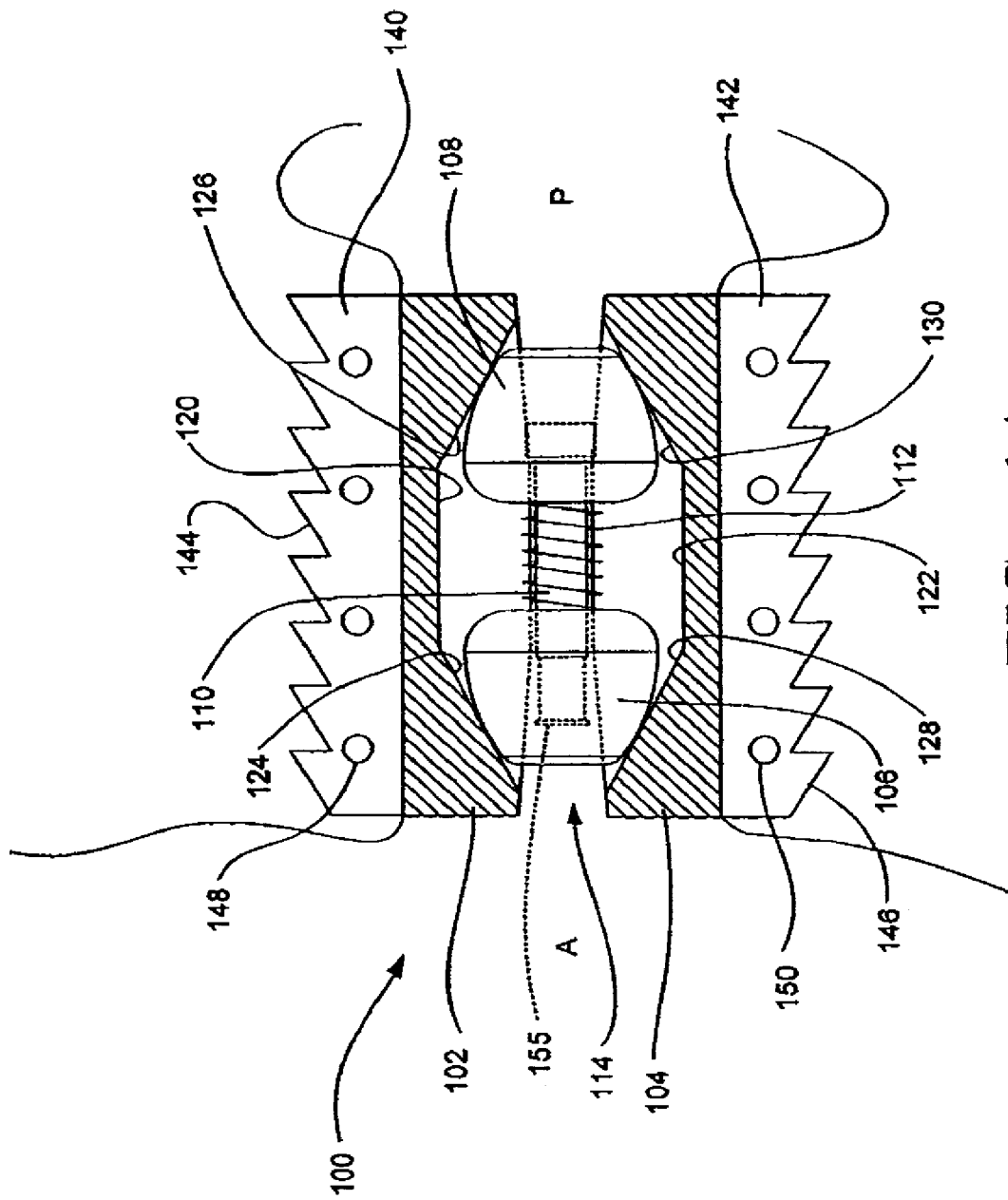
FIG. 1A is a cross-sectional side-view along a sagittal plane of an artificial spinal disk positioned between adjacent vertebrae in accordance with one embodiment of the present invention.
Figure 1B:
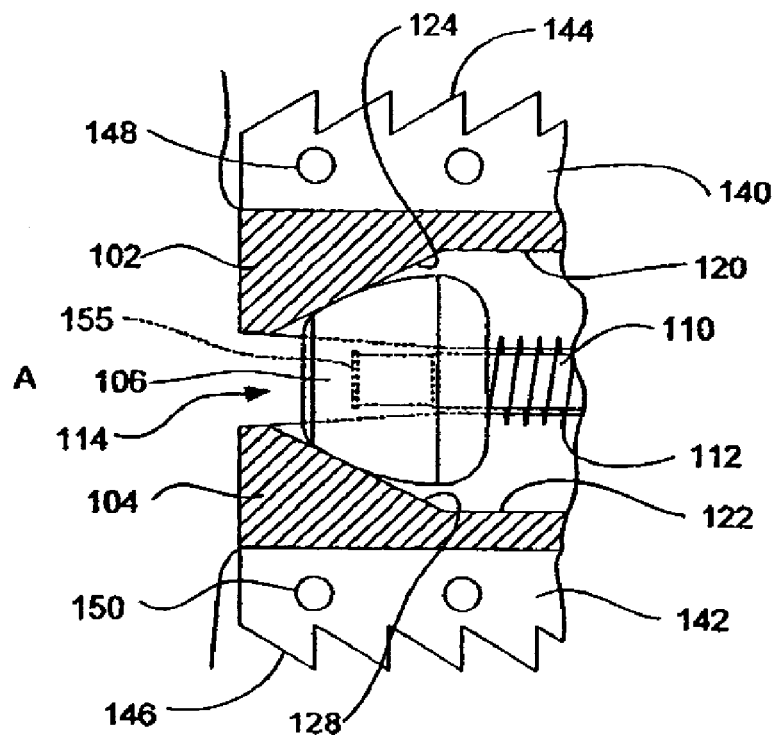
FIG. 1B is an enlarged side view of an anterior end of the artificial spinal disk shown in FIG. 1A.
Figure 1C:
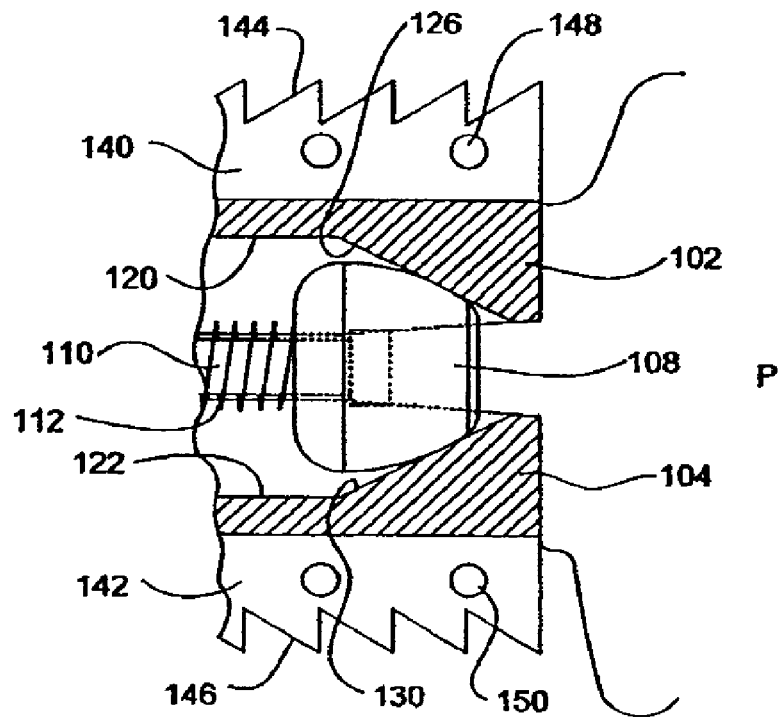
FIG. 1C is an enlarged side view of a posterior end of the artificial spinal disk shown in FIG. 1A.
Figure 1D:
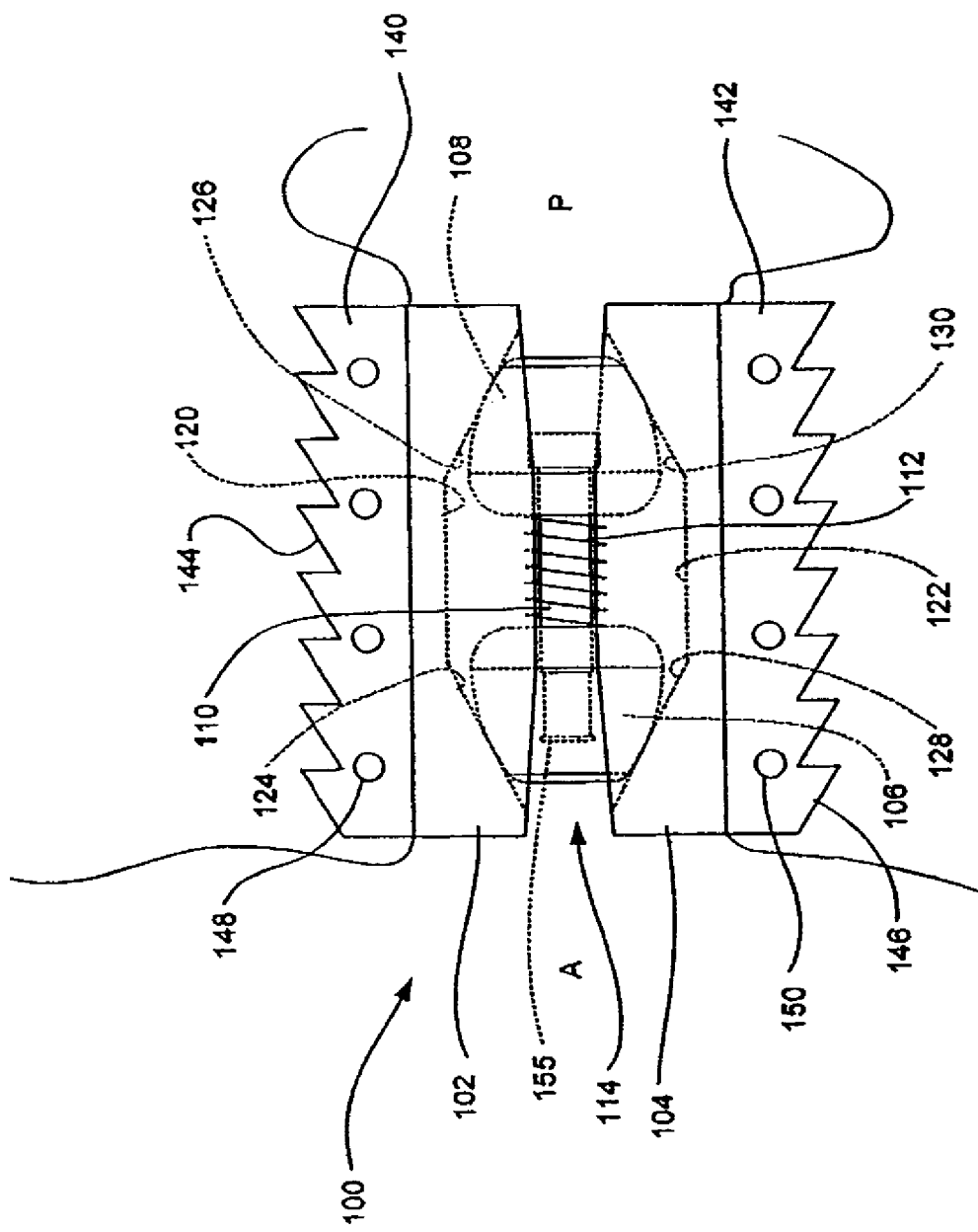
FIG. 1D is a side view of the embodiment of the invention in FIG. 1A with internal structure shown in the dotted lines.
Figure 1E:
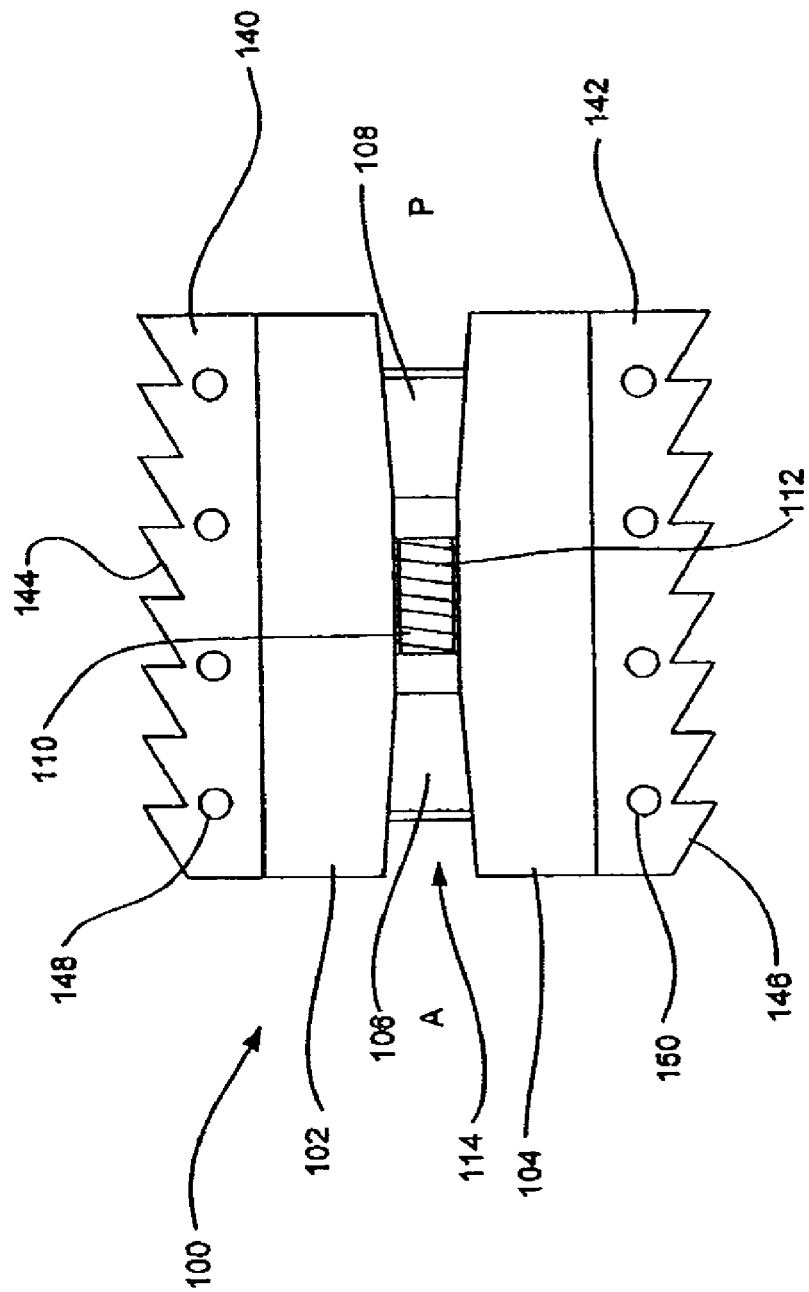
FIG. 1E is a side view of the embodiment of the invention in FIG. 1A.

Systems and methods in accordance with the present invention can comprise one or more artificial spinal disks for replacing a degenerated spinal disk. FIGS. 1A-1C illustrate a cross-section along a sagittal plane of an artificial spinal disk 100 positioned between adjacent vertebrae in accordance with one embodiment of the present invention. The artificial spinal disk 100 comprises an upper housing 102 and a lower housing 104 that combined to form a cavity 114 that partially enclose an anterior spacer 106 and a posterior spacer 108. The spacers 106, 108 are mounted on a shaft 110 of the preferred embodiments. The spacers 106,108 are urged apart by a spring 112 mounted concentrically on the shaft 110. As can be seen in the Figures, the spacers 106, 108 are bell shaped with an inwardly sloping cylinder side that acts as a ramp relative to the upper and lower housings 102, 104. As can be seen in FIG. 5B, the shaft 110 can comprise a plurality of segments of different diameters. Shaft 110 in this embodiment is fixed to spacer 108 and shaft 110 retains spacer 106 between stops. Thus spacer 106 can move relative to shaft 110 and is urged away from spacer 108 by spring 110.

In one embodiment, a cross-section of each of the upper housing 102 and the lower housing 104 along a sagittal plane can have inner cavities or recesses 120, 122 that varies from an anterior end to a posterior end of the housing 102,104 and that have ramps 124, 126 and 128,130 respectively, such that when the upper and lower housing 102,104 are urged together, for example by a compressive or torsional force applied to the artificial spinal disk 100, spacer 106, slides toward spacer 108. It is to be understood that in an alternative embodiment that both spacers 106, 108 can be movably mounted on shaft 110 and thus when a load is placed on artificial spinal disk 100, both spacers 106, 108 can slide towards each other. Accordingly can be seen in FIG. 1A-1C, the cavities or recesses 120, 122 of the upper housing 102 and lower housing 104 can each have a minimum depth at the anterior and posterior ends of the housing 102, 104 and a maximum depth approximately at the center of the housing 102, 104. From a position at the center of the housing 102, 104 and extending outwardly in both directions, the depth of the cavities or recesses 120, 122 decrease in a linear fashion such that ramps 124, 126, and 128, 130 are formed at each of the posterior and anterior ends. In other embodiments, the ramps can vary in a non-linear fashion such that the ramps can have a concave shape or a concave shape or a combinations of shapes.

As can be seen in FIG. 1A, the artificial spinal disk 100 also includes keels 140 and 142 extending from the upper housing 102 and the lower housing 104 respectively. The keels 140 and 142 are directed in this embodiment along a posterior/anterior line. In other embodiments described and depicted herein, the keels can be oriented laterally such that the keels are about perpendicular to the sagittal plane of the body. In other words the lateral keels would be used for method which involved a lateral implantation of the disk 100 relative to the spine.

In the embodiment of FIG. 1A, the keels 140, 142 each have teeth, 144, 146 respectively. For embodiments that are inserted from a posterior to an anterior direction, as depicted in FIG. 1A, the teeth point in a posterior direction with a ramp facing an anterior direction. This configuration allows the keels to be more easily inserted into keel channels cut in the vertebral bodies, and helps to lock the keels in place. In general it is advantageous to have the teeth point in a direction that is opposite to the direction of insertion of the keel into the bone and in this particular situation into the vertebral bodies of the spine.

In the embodiment shown the keels include ports 148 and 150. Bone from, for example, the vertebral bodies can grow thorough the ports and aid in securing the keels and the artificial disk 100 with respect to the vertebral bodies. In addition the keels and the surfaces of the artificial spinal disk 100 can be roughened in order to promote bone in growth into the surfaces of the artificial spinal disk 100. By way of example only, such surfaces can be coated with a bone growth substance such as for example bone morphogenic protein, BMP or hyaluronic acid, HA, or other substance which promotes growth of bone relative to and into the keel, keel ports, and other external surfaces of the disk 100. In addition in another embodiment these surfaces can be coated with cobalt chrome in order to provide a surface for bone-in growth relative to the replacement disk 100.

Figure 2A:
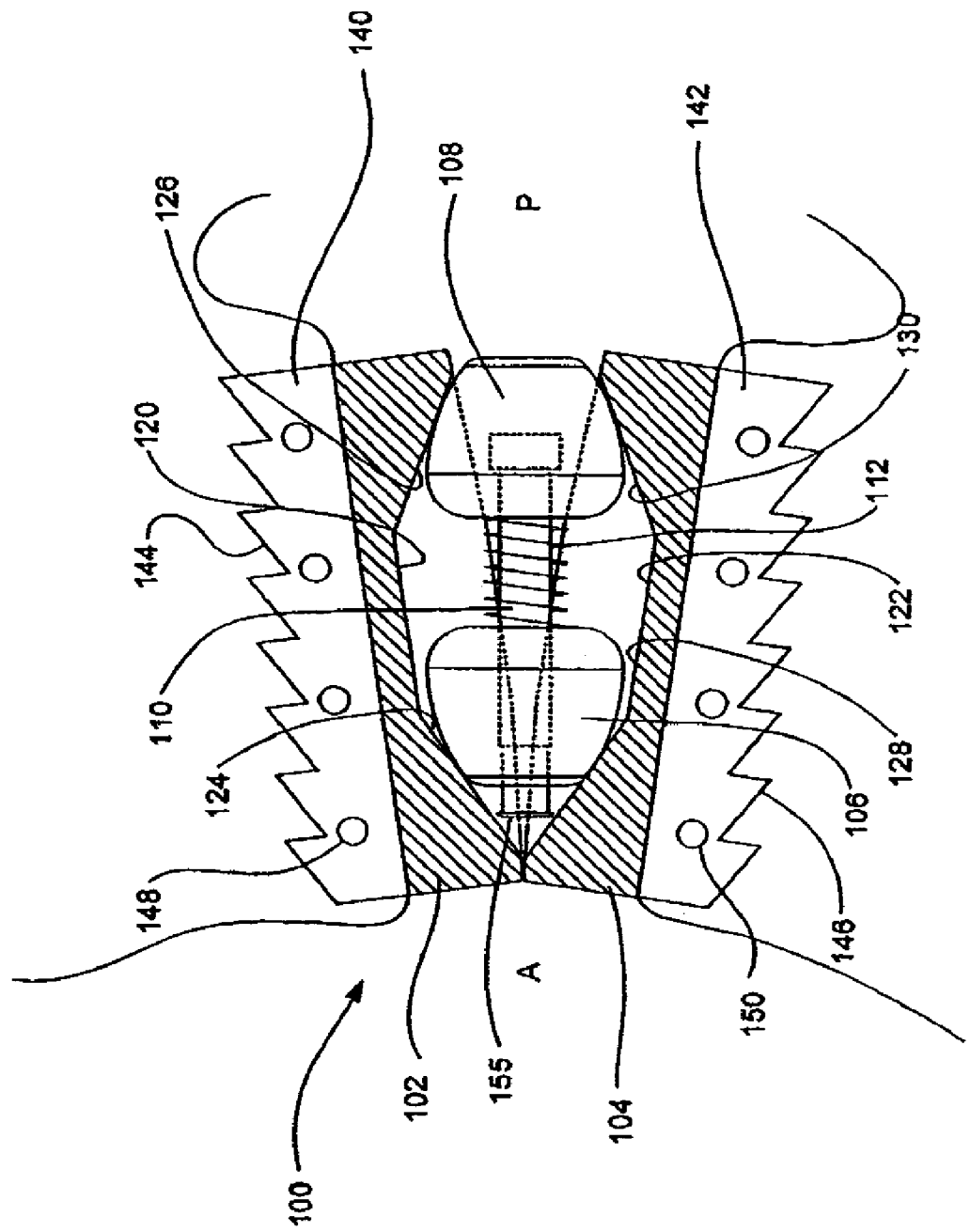
FIG. 2A shows the artificial spinal disk of FIG. 1A during a forward bending motion of a spine.
Figure 2B:
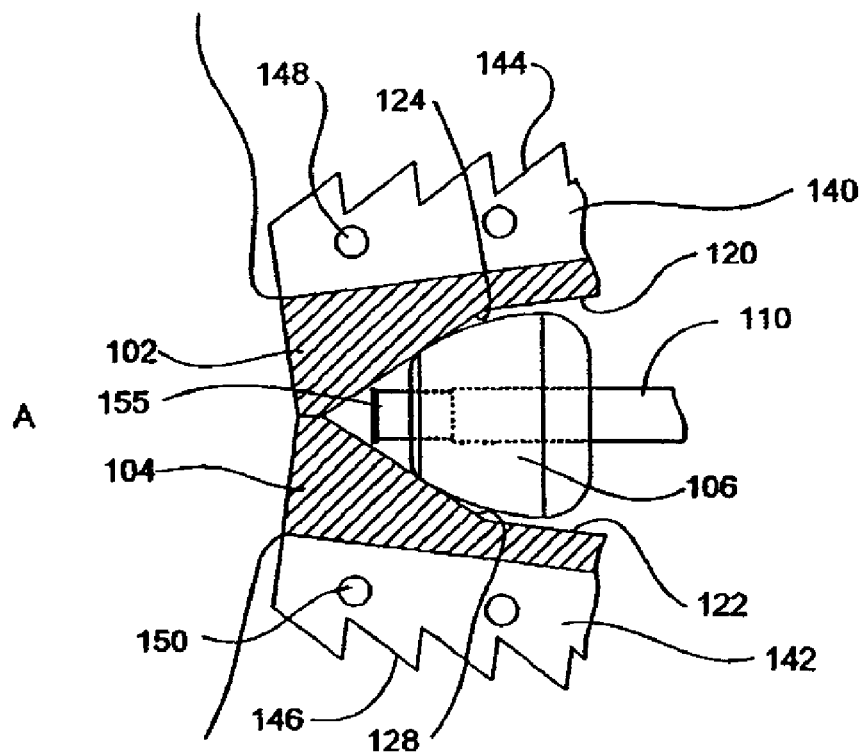
FIG. 2B is an enlarged side view of an anterior end of the artificial spinal disk shown in FIG. 2A.
Figure 2C:
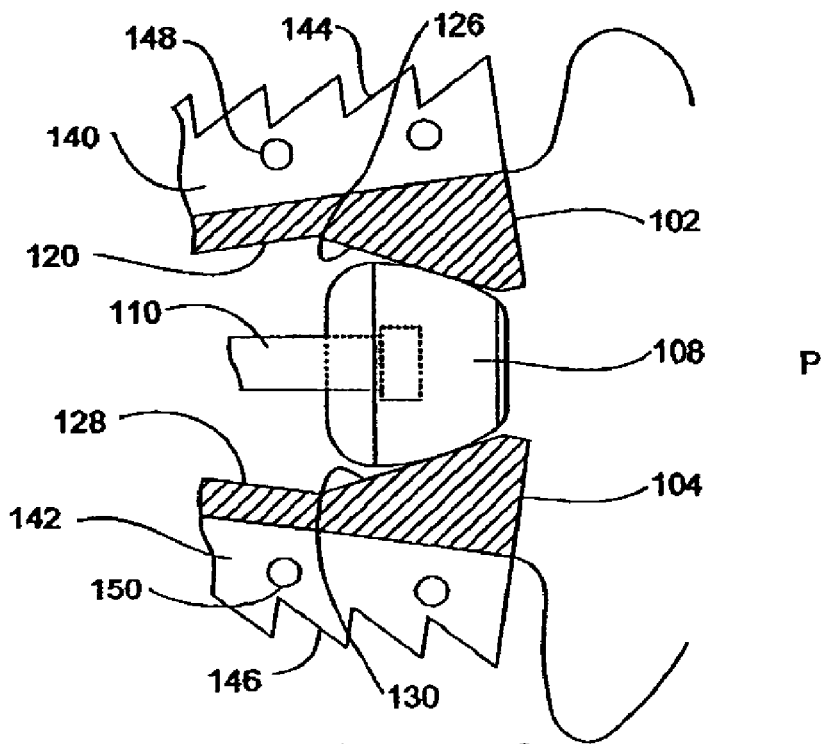
FIG. 2C is an enlarged side view of a posterior end of the artificial spinal disk shown in FIG. 1A.

FIGS. 2A-2C illustrate an artificial spinal disk 100 wherein an anterior end of the upper and lower housings 102,104 are urged together. As a spacer 106 slides toward spacer 108, a gap between the upper housing 102 and the lower housing 104 at the anterior end of the disk 100 lessens. For example, where a patient having an artificial spinal disk 100 bends forward, a bending force is applied to the anterior end of the artificial spinal disk 100, causing the anterior spacer 106 to slide toward a posterior end of the artificial spinal disk 100 by sliding along ramps 124, 128 of the upper and lower housings 102, 104 respectively. The spring 112 is compressed. As shown in FIG. 2B, one end of the shaft 110 passes through the anterior spacer 106 such that the spring 112 is compressed. It is noted that in this embodiment, that although the anterior end of the upper and lower housings of the artificial spinal disk 100 are urged together, that the posterior end of the upper and lower housings maintains a spaced apart distance which is the same as prior to when the force was placed on the disk 100, as for example depicted in FIGS. 1A-1E. That is to say that the maximum height of the disk 100 along the length of the disk 100 does not change. The disk 100 can be compressed at one end, with the other end either being compresses or maintaining the original height. This feature can be advantageous with respect to the anatomy or the spine, as the spine, due to ligaments and other tissues, may allow, for example, an anterior disk space to be compressed together and may not allow an opposed posterior disk space to be expanded. In a natural disk space of the spine, with the anterior disk space compressed, the posterior disk space generally can maintain the same height, or is also compressed. The embodiment of FIGS. 3A, 3B illustrate this feature.

The anterior spacer 106 stops sliding when a component of the bending force urging the anterior spacer 106 to slide along the ramp is balanced by a component of force of the spring 112 on the shaft 110 urging the anterior spacer 106 apart from the posterior spacer 108, or until the upper housing 102 contacts the lower housing 104 and the gap is eliminated. When the bending force is removed from the anterior end of the artificial spinal disk 100, the force of the spring 112 on the shaft 110 causes the anterior spacer 106 to slide toward the anterior end of the artificial spinal disk 110, urging the upper housing 102 and the lower housing 104 apart as the anterior spacer 106 slides on the ramps. The original gap can be restored in this manner by removing the bending force applied to the anterior end of the artificial spinal disk 100. Similarly, as the patient bends backward, a bending force can be applied to the posterior end of the artificial spinal disk 100, causing the posterior spacer 108 and shaft 110 to slide toward the spacer 106 and the anterior end of the artificial spinal disk 100.

The cross-section of the artificial spinal disk 100 shown in FIGS. 1A-2C depict the upper and lower housings being of the same shape. In other embodiments, however, a cross-section of the upper housing 102 can differ from a cross-section of the lower housing 104. For example, the lower housing 104 can be a flat plate substantially conforming to a flat surface of one or more spacers. In still other embodiments, the posterior end of the artificial spinal disk 100 can have a different configuration from the anterior end of the artificial spinal disk 100. For example, where increased stiffness is desired, the posterior end can include a substantially flat portion, or a portion having a steeper ramp for the spacer thereby resisting flexion from bending in the backward direction. One of ordinary skill in the art can appreciate the different devices that can allow various movements between adjacent vertebrae.

Figure 3A:
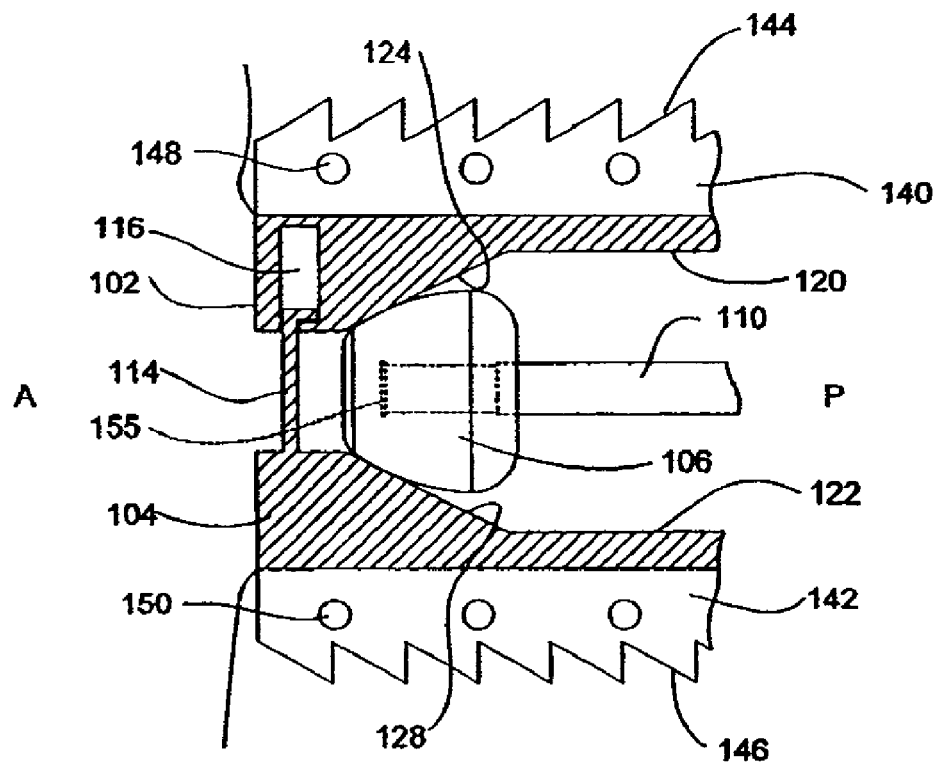
FIG. 3A is a cross-sectional side view along a sagittal plane of an anterior end of an alternative embodiment of an artificial spinal disk of the present invention showing a latch or engagement mechanism that connects a lower housing and an upper housing.
Figure 3B:
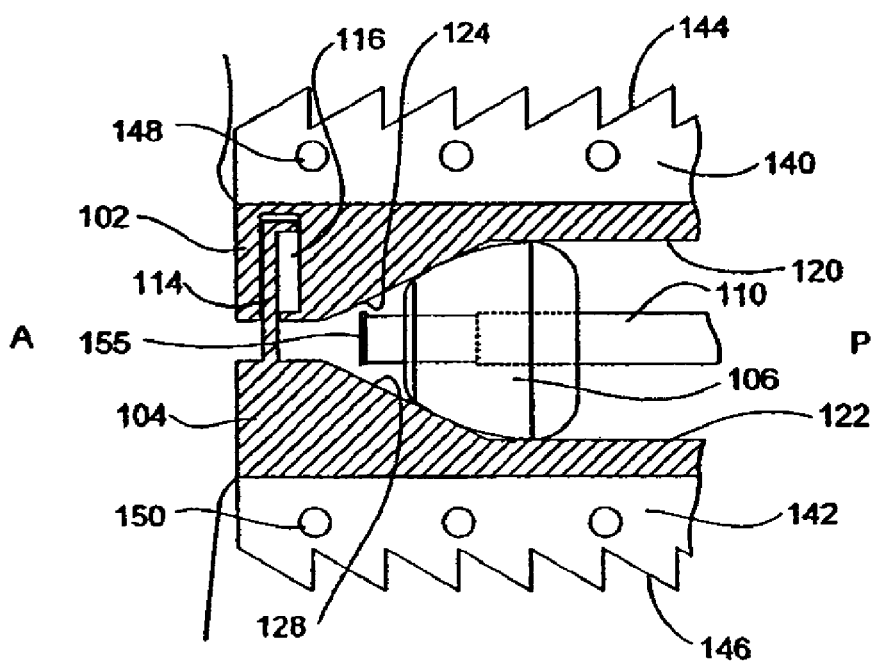
FIG. 3B is a cross sectional side view of an urged-together anterior end of the artificial spinal disk of the alternative embodiment shown in FIG. 3A.

As shown in FIGS. 3A and 3B, the artificial spinal disk 100 can further comprise a clasp 114 or other locking mechanism connecting the upper and lower housings 102,104 together at anterior and posterior ends. A receiving end 116 for receiving the clasp 114 is formed in the opposite housing 102,104 so as to receive the clasp 114. The clasp 114 can be adapted to prevent the gap between the housings 102, 104 from expanding beyond a maximum width, for example at the posterior end, when forward bending causes flexion at the anterior end. As the spring 112 is compressed by the sliding of the anterior spacer 106, the force applied by the spring 112 on both the anterior spacer 106 and the posterior spacer 108 increases. Where no restraint is applied to the posterior end, the posterior spacer 108 can slide further toward the posterior end, causing the gap at the posterior end to increase beyond the original height. The clasp 114 can prevent expansion of the gap beyond a maximum height when a force is applied by the compressed spring 112 to the posterior spacer 108 during forward bending. The clasp 114 can further prevent shifting of the upper housing 102 relative to the lower housing 104. In other embodiments, other mechanisms can be used. For example, the upper housing 102 and lower housing 104 can be tethered together.

The artificial spinal disk 100 are generally anchored or fixed to the vertebrae. Fixation can be achieved, for example, as previously described by, with one or both of the upper and lower housings 102, 104 including a keel 140, 142 which extend therefrom, which keels can include teeth 144, 146 respectively. Appropriate channels can be cut in the upper and lower adjacent vertebrae to receive the keels 140, 142 in order to retain the artificial spinal disk 100 relating to the vertebrae. Fixation can also be accomplished (1) by anchoring using one or more teeth, pegs, or posts extending from the upper and/or lower housing 102,104 and inserted into the vertebrae (2) by promotion of bone-in growth by means of a porous contact surface of each housing 102, 104, or (3) by fixation with screws through ports in the upper and/or lower housings 102, 104. In one embodiment, the top surface of the upper housing 102 can include teeth which can penetrate into the top vertebra, fixing the artificial spinal disk 100 with respect to the top vertebra. Similarly, the bottom surface of the lower housing 104 can include teeth which can penetrate into the bottom vertebra, fixing the artificial spinal disk 100 with respect to the bottom vertebra.

Figure 4:
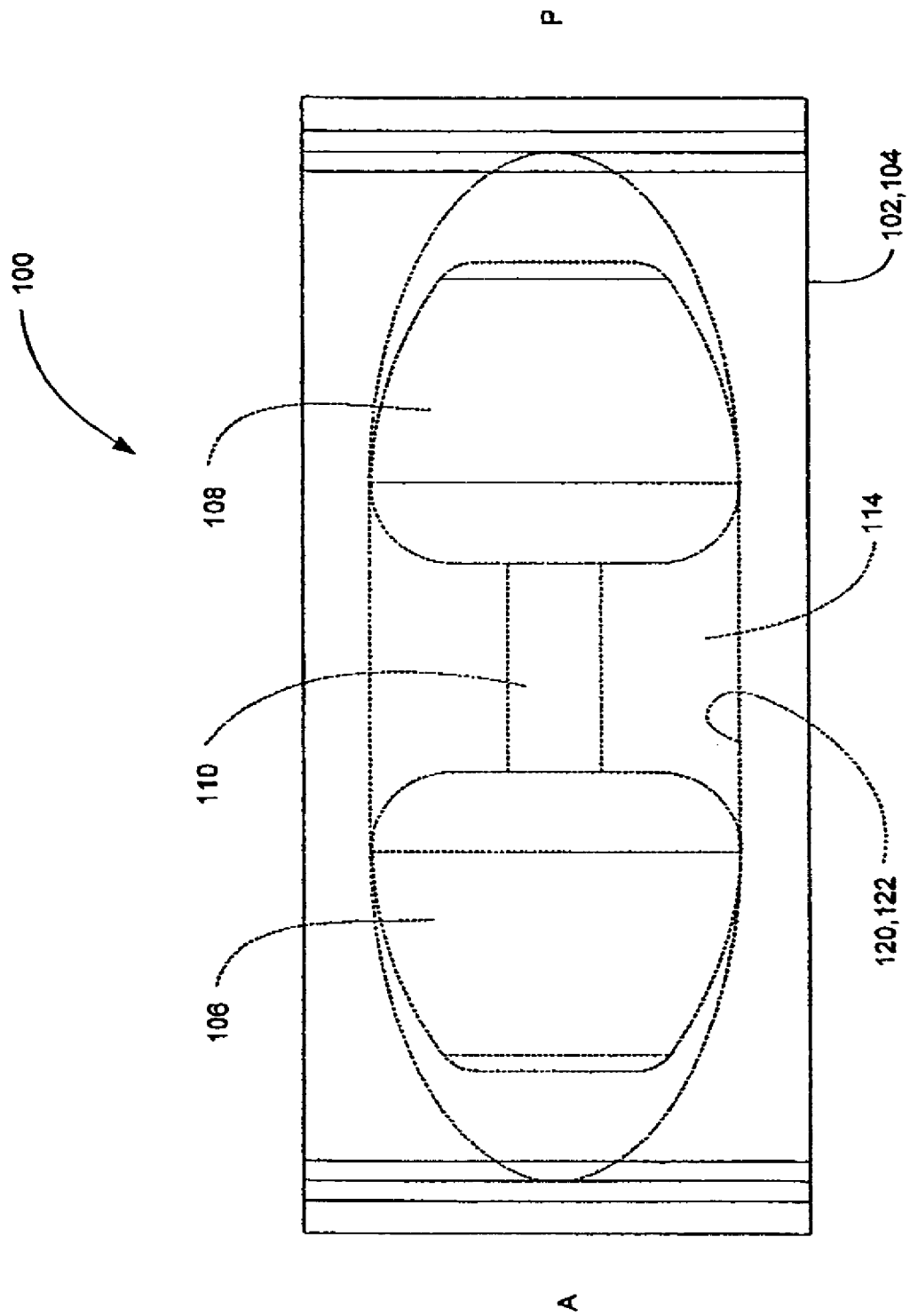
FIG. 4 is a cross-sectional top plan view along a transverse plane of an artificial spinal disk in accordance with the embodiment FIG. 1A of the present invention.

FIG. 4 illustrates a top down view of an artificial spinal device 100 in accordance with one embodiment of the present invention. The upper housing 102 and the lower housing 104 can be substantially rectangular in shape with rounded corners to ease insertion into the disk space if desired. A cross-section of the cavity 114 formed between the housings 102, 104 along the transverse plane can be elliptical in shape such that the sidewalls of the cavity 120, 122 roughly conform to the shape of the spacers 106, 108, limiting shifting of the upper housing 102 relative to the lower housing 104. In other embodiments, the cross-section of the cavities 120, 122 can have a different shape. For example, the cross-section of the cavity can be rectangular. In such a configuration the spacers would be block shaped with upper and lower ramps. Such a configuration would not respond to twisting or torsional forces as well as the embodiment shown in FIG. 4. One of ordinary skill in the art can appreciate the different configurations for the cavity.

Figure 5A:
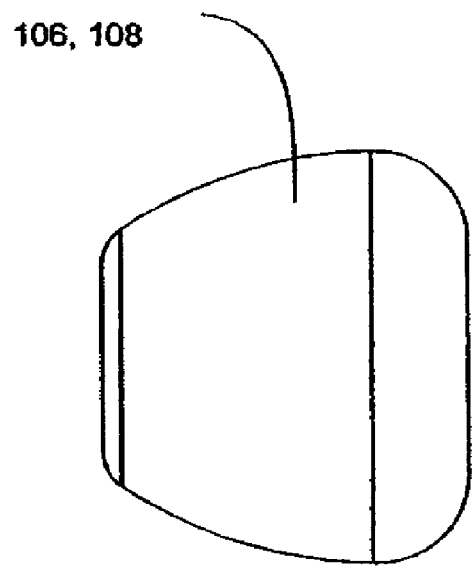
FIG. 5A is a side view of a spacer in accordance with one embodiment of the present invention.
Figure 5B:
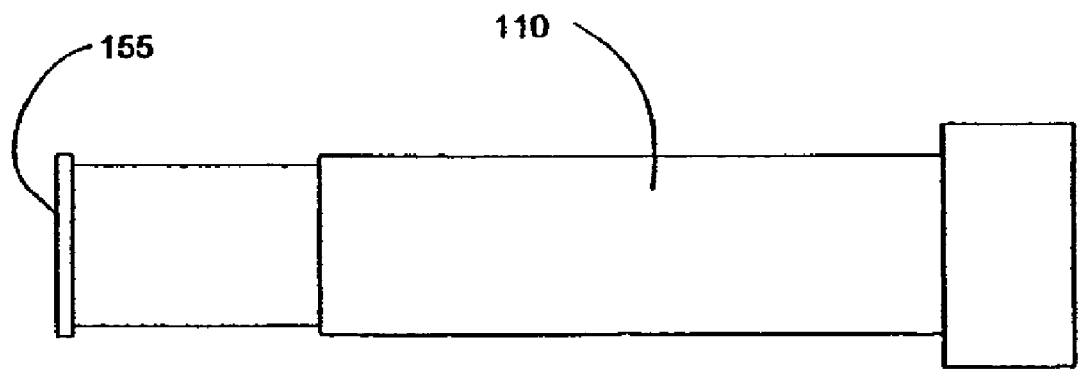
FIG. 5B is a side view of a shaft in accordance with one embodiment of the present invention.

As shown in FIGS. 4 and 5A, the anterior and posterior spacers 106,108 can be substantially ovoid-shaped or bell-shaped. Each spacer 106,108 can be radially symmetrical about an axis along the length of the cavity and can be truncated at a proximal and a distal end, for example to decrease the space occupied by the spacer 106, 108 within the cavity. In other embodiments, the spacer 106, 108 can have a different shape, such as, for example, a wedge shape. A bore can be formed in each spacer 106, 108 for connecting the spacer 106, 108 with the shaft 110. The bore can receive an end of the shaft 110 so that as the spacers 106, 108 are urged together, the spacers more together and relative to the shaft 110. In an alternative embodiment, the anterior spacer 106 can include a tiered cylindrical bore that extends through the anterior spacer 106. This structure can provide stops to limit the motion of the spacer 106 and the shaft 110 relative to each other. In still other embodiments, each spacer 106, 108 can include a collar 155 (FIG. 1A) that is received in a recess of the shaft 110 to limit the motion of the spacers 106, 108 and the shaft 110 relative to each other. One of ordinary skill in the art can appreciate the different means and methods for connecting a shaft with a spacer.

The spacers 106, 108 and housings 102, 104 can be of various shapes and sizes. Thus for example, using imaging prior to surgery, the anatomy of the individual patent can be determined and the artificial spinal disk 100 selected to suit the particular patient. Additionally, during surgery the physician can be provided with a kit having different sized artificial spinal disks 100 to fit the anatomy of the patient.

The upper housing 102 and lower housing 104 and the spacers 106, 108 and shaft 110 can be made of stainless steel, titanium, and/or other bio-compatible metal or metal composite. Each component can be cast, milled, or extruded, for example. Alternatively, the upper housing 102 and lower housing 104 and the spacers 106, 108 and the shaft 110 can be made of a polymer such as polyetheretherketone (PEEK), (as defined below) or other biologically acceptable material. A material can be selected based on desired characteristics. For example, a metal can be selected based on high relative fatigue strength. Many patients with back pain are in their lower forties in age. In such cases, it may be desired that an artificial spinal disk have a fatigue life of at least forty years, extending beyond a patients octogenarian years.

As indicated above, each spacer 106, 108 can be made of a polymer, such as a thermoplastic, and can be formed by extrusion, injection, compression molding and/or machining techniques. Specifically, the spacer 106, 108 can be made of a polyketone such as PEEK.

One type of PEEK is PEEK 450G, which is an unfilled PEEK approved for medical implantation available from Victrex of Lancashire, Great Britain. Other sources of this material include Gharda located in Panoli, India. PEEK 450G has appropriate physical and mechanical properties and is suitable for carrying the physical load exerted by the upper housing 102 and lower housing 104 while providing a smooth, slidable surface. For example in this embodiment PEEK has the following approximate properties:

| Density | 1.3 g/cc |
|---|---|
| Rockwell M | 99 |
| Rockwell R | 126 |
| Tensile Strength | 97 |
| MPaModulus of Elasticity | 3.5 GPa |
| Flexural Modulus | 4.1 Gpa |

The material selected may also be filled. For example, other grades of PEEK available and contemplated include 30% glass-filled or 30% carbon-filled PEEK, provided such materials are cleared for use in implantable devices by the FDA or other regulatory body. Glass-filled PEEK reduces the expansion rate and increases the flexural modulus of PEEK relative to unfilled PEEK. The resulting product is known to be ideal for improved strength, stiffness, or stability. Carbon-filled PEEK is known to enhance the compressive strength and stiffness of PEEK and lower its expansion rate. Carbon-filled PEEK offers wear resistance and load carrying capability.

As will be appreciated, other suitable bio-compatible thermoplastic or thermoplastic polycondensate materials that resist fatigue, have good memory, are flexible and/or deflectable, have very low moisture absorption and have good wear and/or abrasion resistance, can be used without departing from the scope of the invention. Other materials that can be used include polyetherketoneketone (PEKK), polyetherketone (PEK), polyetherketoneetherketoneketone (PEKEKK), and polyetheretherketoneketone (PEEKK), and generally a polyaryletheretherketone. Further, other polyketones can be used, as well as other thermoplastics.

Reference to appropriate polymers that can be used in the spacer can be made to the following documents, all of which are incorporated herein by reference: PCT Publication WO 02/02158 A1, dated Jan. 10, 2002 and entitled Bio-Compatible Polymeric Materials; PCT Publication WO 02/00275 A1, dated Jan. 3, 2002 and entitled Bio-Compatible Polymeric Materials; and PCT Publication WO 02/00270 A1, dated Jan. 3, 2002 and entitled Bio-Compatible Polymeric Materials. Other materials such as Bionate®, polycarbonate urethane, available from the Polymer Technology Group, Berkeley, Calif., may also be appropriate because of the good oxidative stability, biocompatibility, mechanical strength and abrasion resistance.

Other thermoplastic materials and other high molecular weight polymers can be used. One of ordinary skill in the art can appreciate the many different materials with which a spacer 106, 108 having desired characteristics can be made.

Figure 6A:
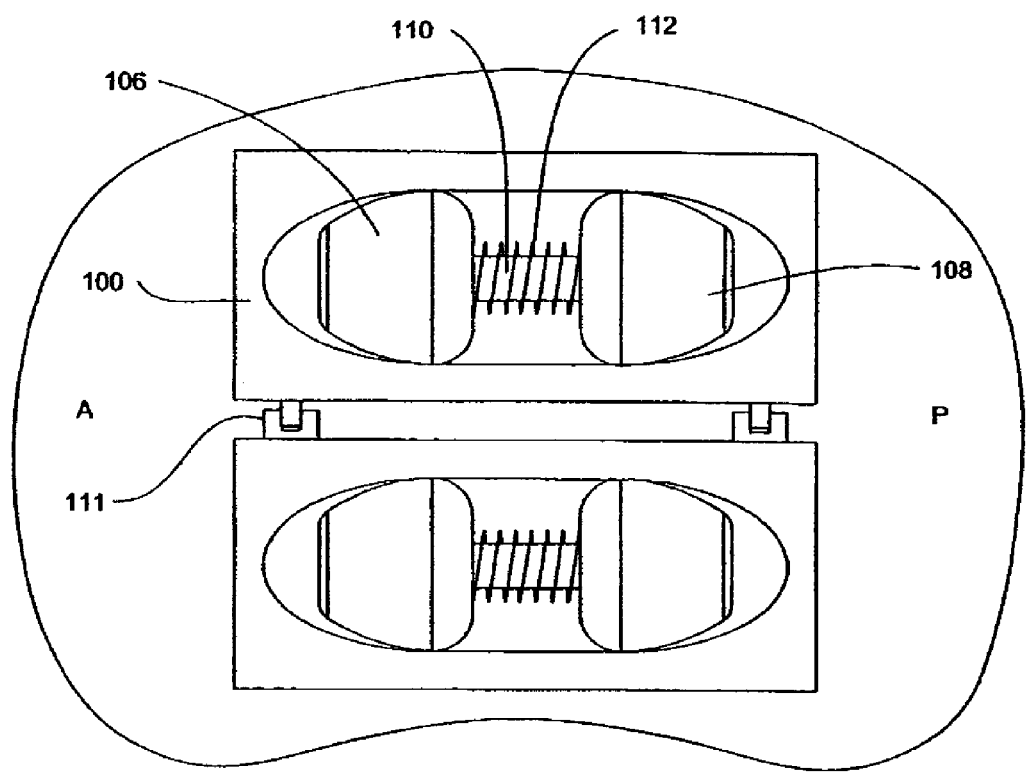
FIG. 6A is a top plan view of a system in accordance with one embodiment of the present invention showing two artificial spinal disks placed side-by-side in substitution for a spinal disk.

FIG. 6A illustrates a top down view of a system comprising two artificial spinal disks 100 in accordance with one embodiment of the present invention. A device or system is typically designed to occupy approximately an entire cross-sectional area of the vertebra so that a spinal load can be distributed over a maximum surface area. A single artificial spinal disk sized to occupy the entire cross-sectional area may complicate surgical insertion that requires implantation of the artificial spinal disk through an open anterior approach. To minimize the incision size, a plurality of artificial spinal disks can form a system in accordance with one embodiment of the present invention for replacing a degenerative spinal disk. By implanting each artificial spinal disk 100 separately, a smaller incision is required, thereby allowing for a posterior approach. As shown in FIG. 6A, the system can comprise two artificial spinal disks 100. However, in other systems three or more artificial spinal disks can be used, or even a single artificial spinal disk. The size of each artificial spinal disk and the number of artificial spinal disks connected can depend on the location of the adjacent vertebrae (for example the defective spinal disk may be a lumbar disk or thoracic disk), the preferences of a surgeon or the preferences of a patient, for example.

First and second artificial spinal disks 100 can be connected together at one or more locations, preferably along opposing surfaces, preventing shifting of one artificial spinal disk 100 relative to the other. The artificial spinal disks 100 can be connected using one or more snaps, pins, screws, hinges or other fastening device 111. One of ordinary skill in the art can appreciate the methods for connecting multiple artificial spinal disks 100 after each disk 100 is separately implanted between adjacent vertebrae.

By way of example, an incision can be made posteriorly from the left or right of the spinous processes. The disk space can be cleaned and tissue removed as required. Then disk 100 can be inserted through the incision. Thereafter, the second disk can be inserted into the disk space through the disk space through the incision. Once the second disk 100 is positioned the two disks can be secured together by for example inserting a pin or screw between aligned eyelets extending form the disks 100 as seen in FIG. 6A.

Figure 6B:
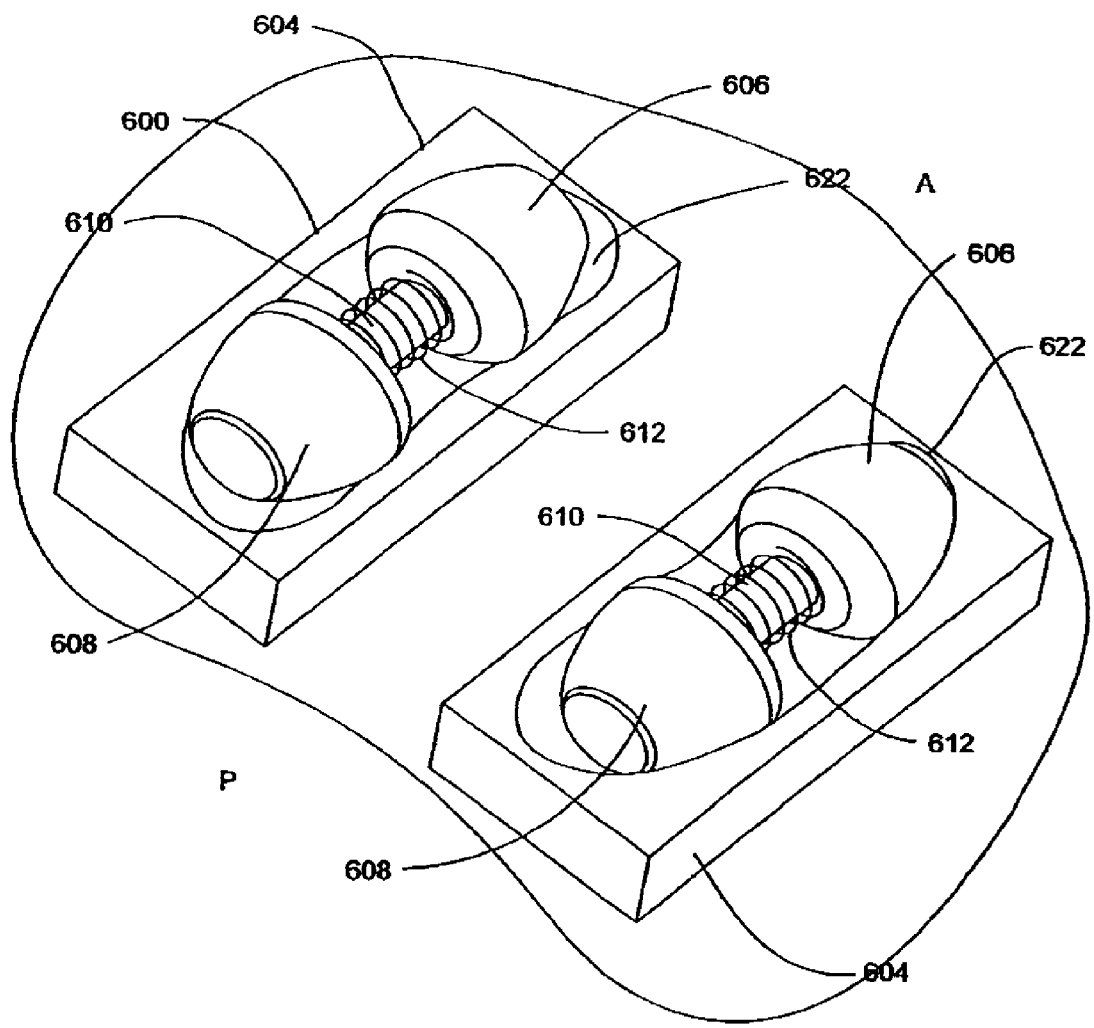
FIG. 6B is a top plan view of another system in accordance with another embodiment of the present invention showing two alternative artificial disks placed side-by-side in substitution for a spinal disk.

As can be seen in FIGS. 6B, 6C in other embodiments, an artificial spinal disk 600 can comprise a first spacer 606 and a second spacer 608, each spacer being positioned at an opposite end of a shaft 610, which shaft is substantially parallel to a sagittal plane. The shaft 610 allows for urging the spacers 606, 608 toward each other. The artificial spinal disk 600 permits flexion from side to side. The artificial spinal disk 600 can comprise an upper housing 102 and a lower housing 104 that together form a "kidney bean" shaped cavity 612. The kidney shaped cavity 612 can accommodate side to side bending with simultaneous twisting or tortional motion of the spine. The separate disks 600 can be implanted and joined together or described above with respect to FIG. 6A.

Figure 7:
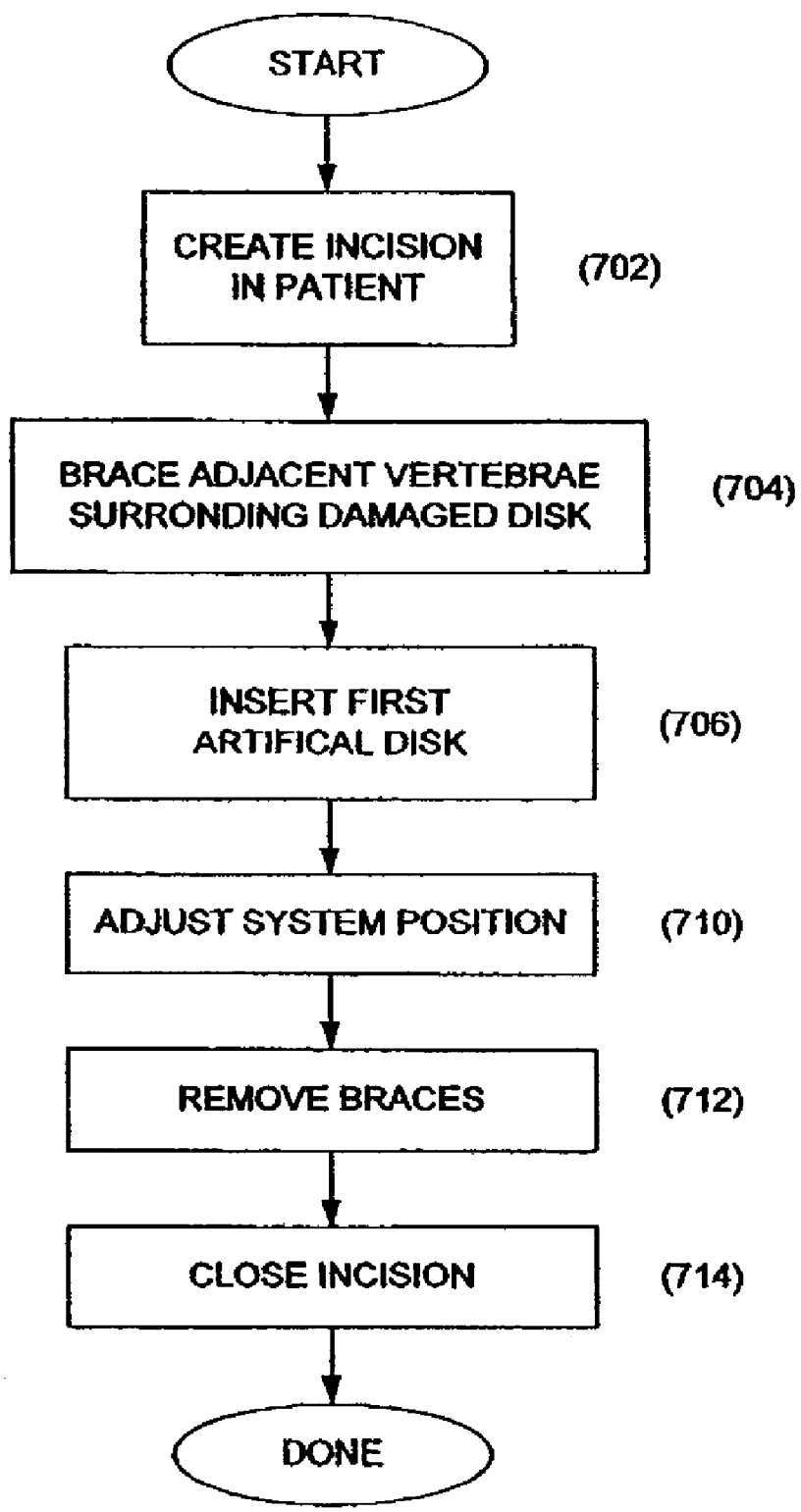
FIG. 7 is a representation of a method for replacing a degenerated spinal disk in accordance with one embodiment of the present invention.
Figure 14:
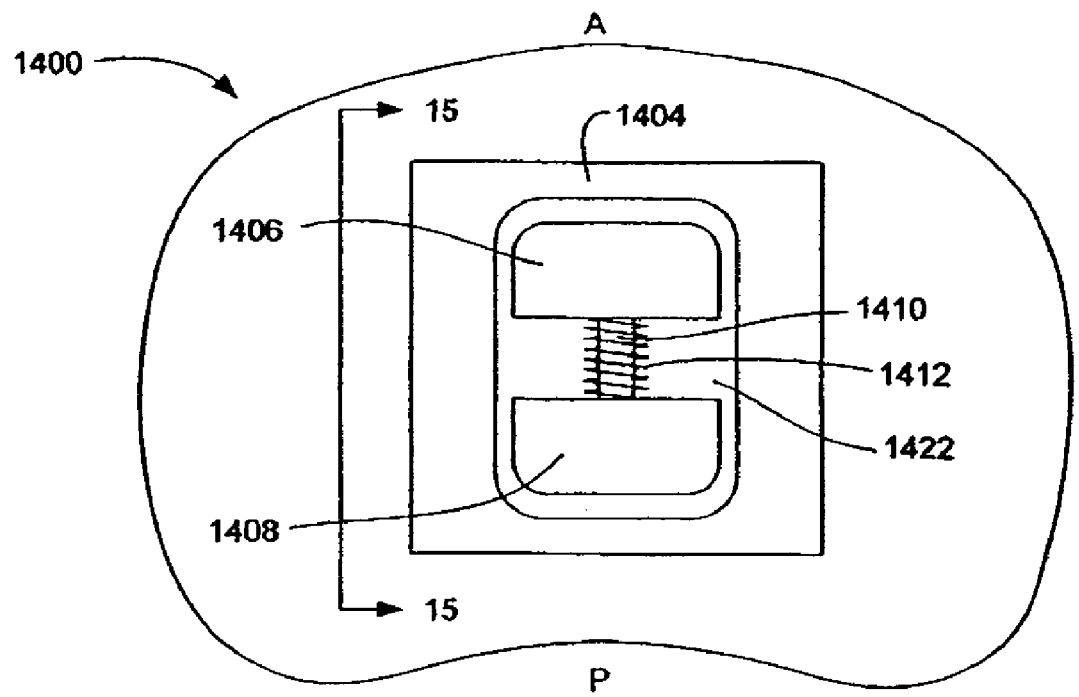
FIG. 14 is yet another an alternative embodiment of the invention with the upper housing removed, and which is insertable laterally into an intervertebral disk space.

FIG. 7 is a block diagram showing steps for performing a method for inserting a disk 100 into a patient in order to replace a degenerated spinal disk or otherwise defective spinal disk in accordance with the present invention and using a posterior, anterior or lateral approach. As shown in first block 700, an artificial spinal disk is selected according to the size of the spinal disk to be replaced and the degree and character of the freedom of movement desired. In one embodiment, a first and second artificial spinal disk 100 as shown in FIGS. 1A-1E can be selected. In an alternative embodiment, a single artificial spinal disk 600 as shown in FIG. 14 can be selected. An incision is made in the patient proximate to the defective spinal disk (step 702), and the spinal disk and surrounding tissues are exposed. The adjacent vertebrae are braced (if required), so that the defective spinal disk can be removed (if required), allowing for replacement by the artificial spinal disks 100 (step 704). An artificial spinal disk 100 can be inserted through the incision and positioned between the adjacent vertebrae (step 706). For this procedure, the nerve and other structures of the spinal column can be retracted out of its way. Minor adjustments in positioning can then be made (step 710) followed by removing the braces (if used) (step 712). The incision is closed (step 714).

Also it is to be understood that as described below, an artificial spinal disk can be inserted laterally into a disk space between two adjacent vertebral bodies. In this method the spine is approached laterally and disk tissue is removed as is appropriate. Then the disk 100 is inserted along a lateral direction.

Other methods of insertion include having the disk 100 disassembled prior to insertion. For this method, an upper or a lower housing 102, 104 can first be inserted and either loosely positioned or fixed to a vertebra, followed by a first spacer 106, a shaft 110, and a second spacer 108. The housing 102, 104 can then be joined or snapped together using the mechanism shown in FIGS. 3A, 3B. The procedure can be repeated for multiple artificial spinal disks.

FIGS. 8-15 depict artificial spinal disks that are preferably inserted using a lateral approach to the spine along a direction that is substantially perpendicular to a sagittal plane of the spine.

Figure 8:
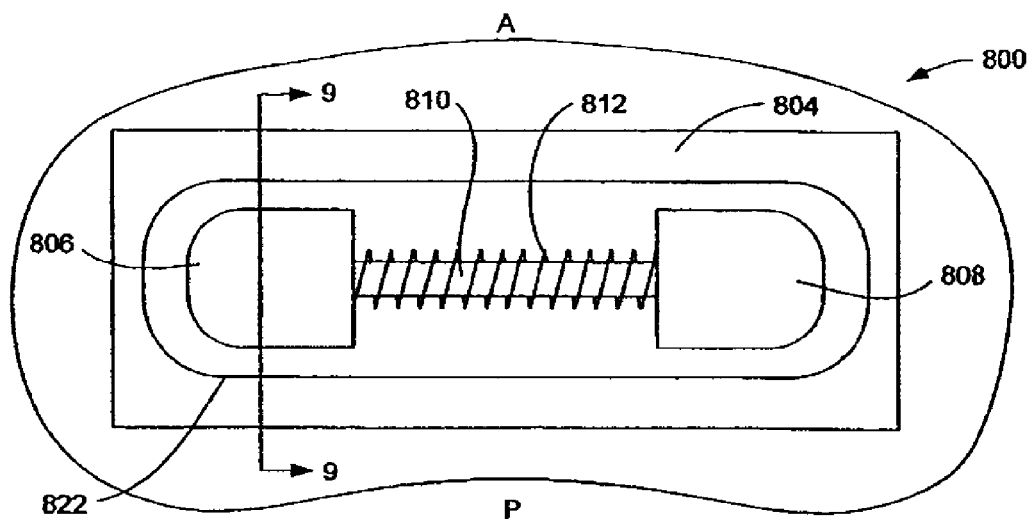
FIG. 8 is a plan view of an embodiment of the invention with the upper housing removed and, which is insertable laterally into an intervertebral disk space.
Figure 9:
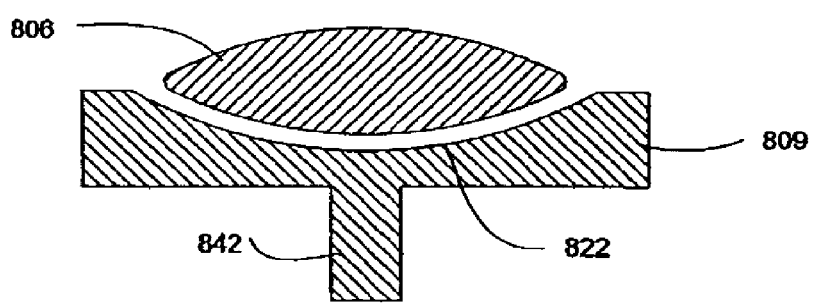
FIG. 9 is a cross-section taken through line 9-9 of FIG. 8.
Figure 10:
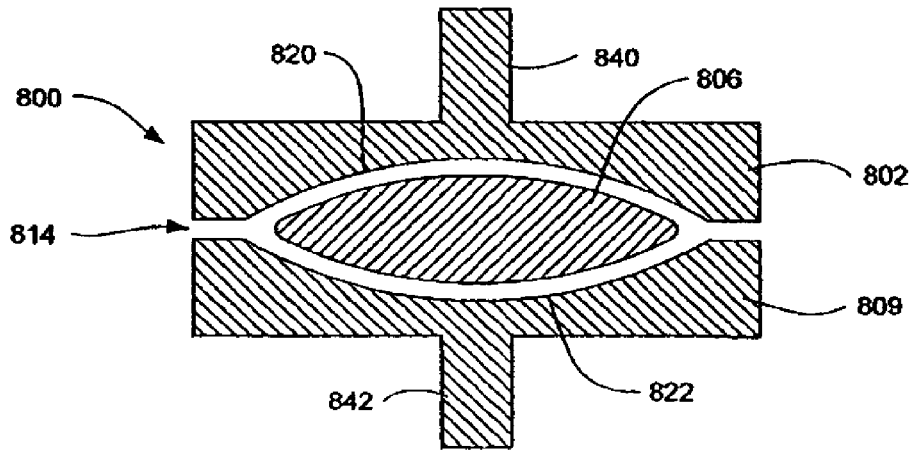
FIG. 10 is cross-section taken through line 9-9 of FIG. 8 with an upper housing depicted.

In these embodiments, elements that are similar to the elements of prior embodiments are similarly numbered. In FIGS. 8-10 an artificial spinal disk 800 includes upper and lower housings 802 and 804 which together define a cavity 814 that partially enclose lateral spacers 806 and 808. The spacers 806 and 808 are mounded on a shaft 810 with a spring 812 moved over the shaft so as to urge spacers 806 and 808 apart. The spacers in this embodiment are larger, broader and flatter than the spacers in prior embodiments in order to carry and spread out the load from the spinal column.

As can be seen in FIGS. 9 and 10, the spacers 802, 804 are somewhat elliptical or football shaped in cross-section. In the plan view of FIG. 8, the spacers 802, 804 are depicted as somewhat wing-tip shaped. The spacers 806, 808 are received in cavities or recesses 820, 822 provided in the upper and lower housings 802, 804 respectively. These recesses are similar to recesses 120, 122 although somewhat flatter. These recesses 820, 822 have the same cross-section as do recesses 120, 122 as seen in FIG. 1A in that each includes a ramp at either end of the recess with a central portion having a greater depth than the ramped portions of the recesses. The spacers 806, 808 are similarly mounted on the shaft 810 as are spacers 106, 108 mounted on shaft 110.

The upper and lower housings 802, 804 further include keels 840 and 842 which can be similar in design as keels 140 and 142. In this embodiment, however, the keels 840, 842 are provided along a lateral orientation with respect to the spine. In order words, the keels are provided on disk 800 so that after disk 800 is implanted, the keels are substantially perpendicular to the sagittal plane of the spine. The keels 802, 804 are preferably provided parallel to and over the shaft 810 in order to balance the load of the spine on the disk 800. Such an arrangement provides stability to the disk 800 with respect to bending of the spine from flexion to extension in the sagittal plane.

The present embodiment is preferably implanted laterally or substantially perpendicular to the sagittal plane of the spine. Accordingly the method of implantation is similar to that described in FIG. 7 except that the approach to the spine is laterally instead of a posterior approach.

Figure 11:
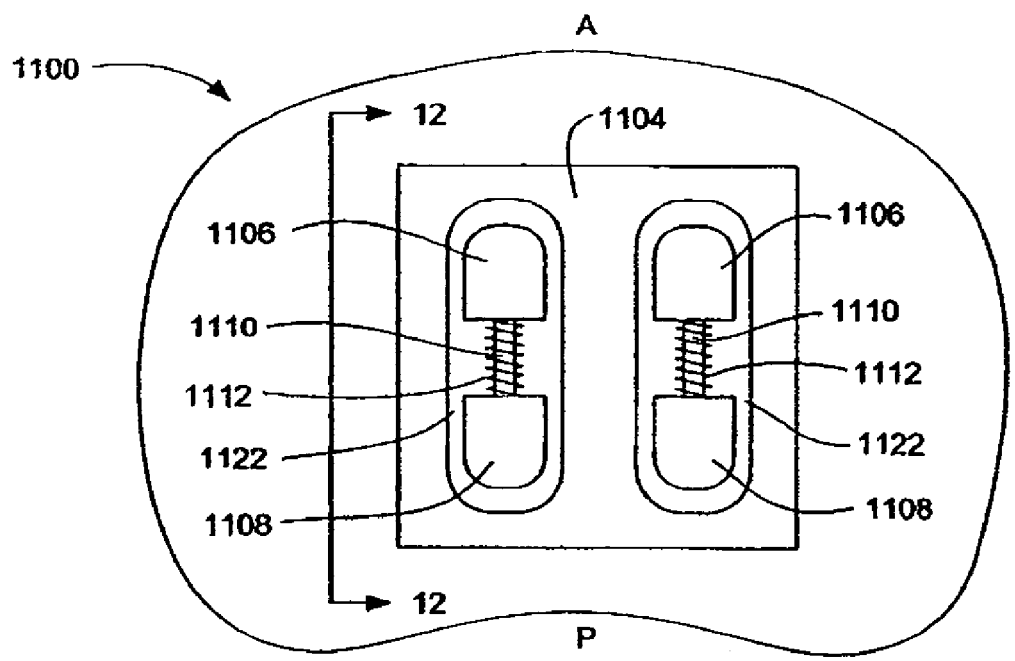
FIG. 11 is an alternative embodiment of the invention with the upper housing removed, and which is insertable laterally into an intervertebral disk space.
Figure 12:
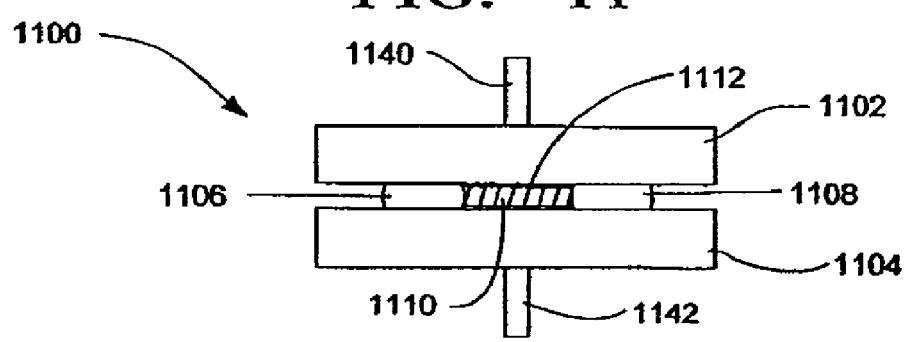
FIG. 12 is a cross-section taken through line 12-12 of FIG. 11 with an upper housing depicted.
Figure 13:
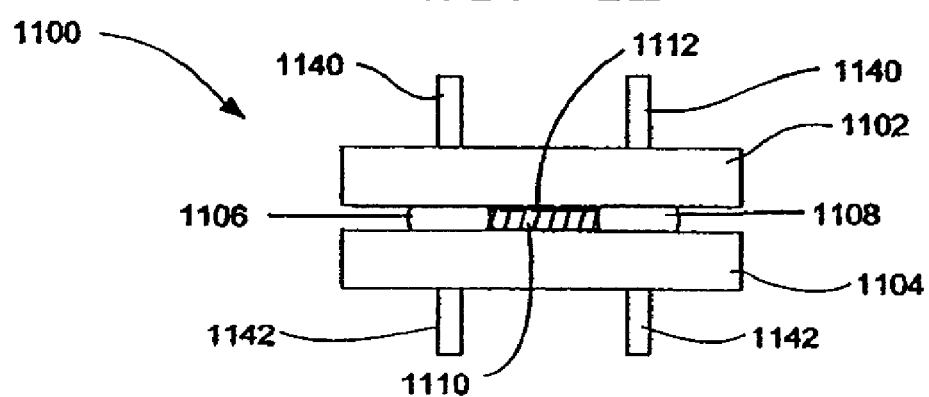
FIG. 13 is a cross-section similar to FIG. 12 with the upper and lower housings each having two keels.

FIGS. 11-13 depict another embodiment of the invention that is preferably implanted laterally or substantially perpendicularly to the sagittal plane of the spine. In this embodiment elements similar to elements of prior embodiments are similarly numbered. In this embodiment, however, each implant includes two pairs of spacers 1106, 1108 which are mounted on substantially parallel shafts 1110 and urged apart by springs 1112. It is to be understood that the shafts 1110 can be other than parallel and be within the spirit and scope of the invention. For example the shafts can be placed in somewhat of a "v" shape with the base of the "v" pointed to the posterior of the spine and the open end of the "v" pointed to the anterior of the spine. The spacers 1106, 1108 are preferably similar in shape to the bell shaped spacers in FIG. 1. The recess 1122 is similar in shape, having the ramps at the ends as the recesses 122 in the first disk embodiment 100. The disk 1100 operates in the same manner as the disk 100 or to be more specific, similar to two disks 100, placed side-by-side. As the disk 1100 can be implanted laterally, there is no need to have the disk divided into two portions as is the case with the disk of FIG. 6A which is implanted with a posterior approach. Further it is to be understood that the disk 1100 can also be inserted using an anterior approach.

As can be seen in FIGS. 12, 13 the lateral implantation approach is preferred due to the laterally oriented keels 1140, 1142. These keels are similarly oriented as are the keels depicted in FIGS. 9, 10. In FIG. 13 both the upper and the lower housings include a pair of keels 1140, 1142 respectively, with the keels preferably located over the spacers 1106, 1108. The keels can have the same ports and bone in growth enhancements as the other keels described above.

Figure 15:
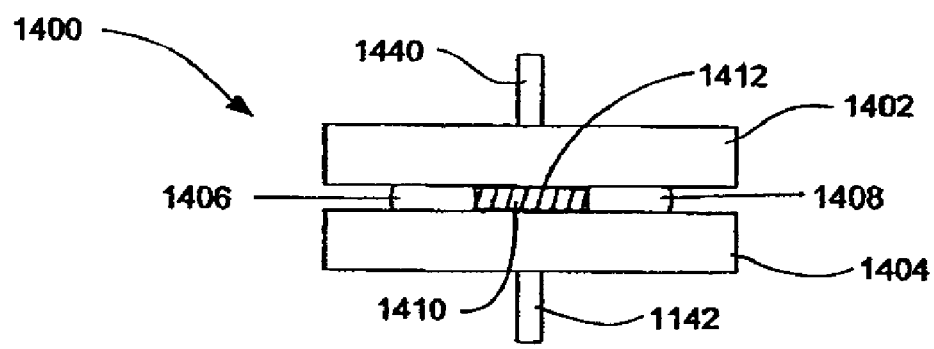
FIG. 15 is a cross-section taken thought line 15-15 of FIG. 14 with an upper housing depicted.

With respect to FIGS. 14, 15 the artificial spinal disk 1400 includes elements that are similar to those described above and these elements are similarly numbered. This embodiment is also preferably implanted using a lateral approach although an anterior approach can also be used. The embodiment of these figures has spacers 1406, 1408 which are similar in design to the spacers of the embodiment of FIG. 8-11 with the exception that the shaft 1410 and spring 1412 are oriented along an anterior/posterior direction and not laterally as shown in FIG. 8. The spacers 1406, 1408 are received in recess 1422. This embodiment also includes laterally disposed keels 1440, 1442 with all of the above advantages attendant with laterally disposed keels.

It is to be noted that in a number of these Figures the implants are illustrated against a kidney-shaped background that is representative of the plan view shape of the disk space between vertebral bodies.

The foregoing description of preferred embodiments of the present invention has been provided for the purposes of illustration and description. It is not intended to be exhaustive or to limit the invention to the precise forms disclosed. Many modifications and variations will be apparent to one of ordinary skill in the relevant arts. The embodiments were chosen and described in order to best explain the principles of the invention and its practical application, thereby enabling others skilled in the art to understand the invention for various embodiments and with various modifications that are suited to the particular use contemplated. Other features, aspects, and objects of the invention can be obtained from a review of the specification, the figures, and the claims. It is intended that the scope of the invention be defined by the claims and their equivalence.

The invention claimed is:

1. An artificial replacement disk that is positionable between vertebrae comprising:
   an upper housing including an upper cavity;
   a lower housing including a lower cavity;
   a first spacer and a second spacer, said first and second spacers mounted on a shaft with a biasing member located between the first and the second spacers, the biasing member being configured to urge said first and second spacers apart; and
   said first and second spacers partially located in said upper cavity and partially located in said lower cavity.

2. The disk of claim 1,
   wherein the first and second spacers are elliptical in cross-section.

3. The disk of claim 1, wherein at least one of the upper and lower housings comprises a keel extending from an outwardly facing surface.

4. The disk of claim 1, wherein at least one of the upper and lower housings comprises an outer facing surface and a keel extending from the outer facing surface, the keel extending about perpendicular to the outer facing surface.

5. The disk of claim 1, wherein at least said first spacer and said second spacer includes a ramp configured to move relative to a ramp on at least one of said upper cavity and said lower cavity.

6. The disk of claim 1, wherein when the upper housing and the lower housing are urged together, one of the first spacer and the second spacer moves toward the other of the first spacer and the second spacer.

7. The disk of claim 1, wherein at least one of the first spacer and the second spacer includes a ramp.

8. The disk of claim 1, wherein at least one of the first spacer and the second spacer is oval-shaped.

9. The disk of claim 1, wherein the biasing member is a coil spring.

10. The disk of claim 1, wherein the first spacer is configured to slide axially along the shaft.

11. The disk of claim 1, wherein the first and second spacers are spaced apart by a gap distance, and wherein when the upper plate and the lower plate are urged together, the urging of the biasing mechanism is overcome such that the gap distance between the first spacer and the second spacer decreases.

12. An artificial replacement disk that is positionable between vertebrae comprising:
    an upper housing including an upper cavity;
    a lower housing including a lower cavity;
    a first spacer and a second spacer, said first and second spacers mounted on a shaft with a biasing member located between the first and the second spacers, the biasing member being configured to urge said first and second spacers apart; and
    said first and second spacers partially located in said upper cavity and partially located in said lower cavity; and
    wherein the first and second spacers are oval in cross-section.

13. The disk of claim 12, wherein at least one of the first spacer and the second spacer includes a ramp.

14. The disk of claim 12, wherein at least one of the first spacer and the second spacer is oval-shaped.

15. The disk of claim 12, wherein the biasing member is a coil spring.

16. The disk of claim 12, wherein the first spacer is configured to slide axially along the shaft.

17. The disk of claim 12, wherein the first and second spacers are spaced apart by a gap distance, and wherein when the upper plate and the lower plate are urged together, the urging of the biasing mechanism is overcome such that the gap distance between the first spacer and the second spacer decreases.

18. An artificial replacement disk that is positionable between vertebrae comprising:
    an upper housing including an upper cavity;
    a lower housing including a lower cavity;
    a first spacer and a second spacer, said first and second spacers mounted on a shaft with a resisting member located between the first and the second spacers, the resisting member being configured to urge said first and second spacers apart; and
    said first and second spacers partially located in said upper cavity and partially located in said lower cavity,
    wherein when the upper housing and the lower housing are urged together, said first spacer and said second spacer move relative to each other.

19. An artificial replacement disk that is positionable between vertebrae comprising:
    an upper housing including an upper cavity;
    a lower housing including a lower cavity;
    a first spacer and a second spacer;
    a shaft, the first and the second spacers being mounted on the shaft; and
    a resisting member disposed between the first and the second spacers, the resisting member applying a biasing force against the first and second spacers to bias the spacers apart from each other; and
    the first and second spacers being partially located in said upper cavity and partially located in said lower cavity.

20. The disk of claim 19, wherein the biasing member is a coil spring.

* * * * *

UNITED STATES PATENT AND TRADEMARK OFFICE
CERTIFICATE OF CORRECTION

| | | |
|---|---|---|
| PATENT NO. | : 7,837,734 B2 | Page 1 of 1 |
| APPLICATION NO. | : 11/734681 | |
| DATED | : November 23, 2010 | |
| INVENTOR(S) | : Zucherman et al. | |

It is certified that error appears in the above-identified patent and that said Letters Patent is hereby corrected as shown below:

In Column 12, Line 49, in Claim 20, delete "biasing" and insert --resisting--, therefor.

Signed and Sealed this
Fourteenth Day of June, 2011

David J. Kappos
*Director of the United States Patent and Trademark Office*